United States Patent
Lee et al.

(10) Patent No.: US 10,125,367 B2
(45) Date of Patent: Nov. 13, 2018

(54) COMPOSITION FOR PREVENTING OR TREATING ATOPIC DERMATITIS COMPRISING X-SHAPE DNA STRUCTURE AS ACTIVE INGREDIENT

(71) Applicant: THE CATHOLIC UNIVERSITY OF KOREA INDUSTRY-ACADEMIC COOPERATION FOUNDATION, Seoul (KR)

(72) Inventors: Joo Young Lee, Seoul (KR); Gabsik Yang, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/562,894

(22) PCT Filed: Apr. 6, 2016

(86) PCT No.: PCT/KR2016/003595
§ 371 (c)(1),
(2) Date: Nov. 20, 2017

(87) PCT Pub. No.: WO2016/163751
PCT Pub. Date: Oct. 13, 2016

(65) Prior Publication Data
US 2018/0080029 A1   Mar. 22, 2018

(30) Foreign Application Priority Data
Apr. 7, 2015 (KR) .......................... 10-2015-0048953

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 48/00* | (2006.01) | |
| *A23L 33/13* | (2016.01) | |
| *A61K 8/60* | (2006.01) | |
| *A61Q 19/00* | (2006.01) | |
| *C12N 15/117* | (2010.01) | |
| *C12N 5/00* | (2006.01) | |

(52) U.S. Cl.
CPC .......... *C12N 15/1136* (2013.01); *A23L 33/13* (2016.08); *A61K 8/606* (2013.01); *A61K 48/00* (2013.01); *A61Q 19/00* (2013.01); *C12N 15/113* (2013.01); *C12N 15/117* (2013.01); *A23V 2002/00* (2013.01); *C12N 2310/17* (2013.01); *C12N 2310/50* (2013.01); *C12N 2310/52* (2013.01)

(58) Field of Classification Search
None
See application file for complete search history.

(56) References Cited

U.S. PATENT DOCUMENTS

| | | | | |
|---|---|---|---|---|
| 8,486,621 | B2 * | 7/2013 | Luo ........................ | C12N 15/10 435/6.1 |
| 9,393,199 | B2 * | 7/2016 | Irvine .................. | A61K 9/5146 |
| 2007/0117177 | A1 * | 5/2007 | Luo ........................ | C12P 21/00 435/68.1 |
| 2011/0293705 | A1 * | 12/2011 | Irvine .................. | A61K 9/5146 424/450 |
| 2015/0099692 | A1 | 4/2015 | Kim et al. | |

FOREIGN PATENT DOCUMENTS

| | | |
|---|---|---|
| KR | 10-2015-0001222 A | 1/2015 |
| KR | 10-2015-0031413 A | 3/2015 |

OTHER PUBLICATIONS

International Search Report for PCT/KR2016/003595 dated Sep. 23, 2016 from Korean Intellectual Property Office.
Jassies-Van Der Lee, A. et al., "The Immunostimulatory Effect of CpG Oligodeoxynucleotide on Peripheral Blood Mononuclear Cells of Healthy Dogs and Dogs with Atopic Dermatitis", The Veterinary Journal, 2014, vol. 200, pp. 103-108.
Um, S. H. et al., "Enzyme-catalysed Assembly of DNA Hydrogel", Nature Materials. 2006. vol. 5, pp. 797-801.

* cited by examiner

*Primary Examiner* — Sean McGarry
(74) *Attorney, Agent, or Firm* — Revolution IP, PLLC

(57) ABSTRACT

The present invention relates to a pharmaceutical composition for preventing or treating atopic dermatitis, the pharmaceutical composition including, as an active ingredient, X-shaped DNA ($X_L$-DNA) formed by complementary binding of oligonucleotides having nucleotide sequences of SEQ ID NO: 1 to SEQ ID NO: 4. When the pharmaceutical composition is subcutaneously injected into an animal model of atopic dermatitis, effects of easing skin lesions, such as erythema, bleeding and edema, and the like, and ear edema, and reducing expression of immunoglobulin E (IgE) are exhibited. In this regard, the composition can be used as a pharmaceutical composition, a health food, or a cosmetic for atopic dermatitis.

8 Claims, 3 Drawing Sheets

Specification includes a Sequence Listing.

COMPOSITION FOR PREVENTING OR TREATING ATOPIC DERMATITIS COMPRISING X-SHAPE DNA STRUCTURE AS ACTIVE INGREDIENT

TECHNICAL FIELD

The present invention relates to a composition for preventing or treating atopic dermatitis, the composition including, as an active ingredient, X-shaped DNA formed by complementary binding of four oligonucleotides.

BACKGROUND ART

Atopy is a word of the Greek origin which means "abnormal reaction" or "being strange", and refers to allergic symptoms that appear in skin, respiratory mucosa, ocular mucosa, intestinal mucosa, and the like in individuals with an atopic predisposition.

In particular, atopic dermatitis which is a representative type of skin diseases in people with atopic allergies causes skin irritation and itching. Atopic dermatitis also causes dry and sensitive skin, and gives people with atopic dermatitis an unpleasant feeling. Atopic dermatitis is reported to occur mainly from the inside of joint, such as the inside of elbow, back of knee and neck.

Such atopic dermatitis is reported to be present in about 0.5% to about 1% of the whole population. In children (infants), about 5% to about 10% suffer from atopic dermatitis, and even after they become adults, about 20% to about 25% of them suffer from persistent atopic dermatitis.

In particular, atopic dermatitis can continuously cause a lot of pain, and problems, such as the skin that is itchy and scratched all day and night, a broken night's sleep, the skin that becomes hideous, causing growth and development problems of young children and their noncompliance to society, can occur.

Recently, due to diversification of living environment associated with diversified social life influenced by environmental factors and mental stress, many patients with atopic dermatitis are present.

In particular, regarding factors that aggravate such atopic dermatitis, such as dry skin, changes in ambient temperature and humidity, severe exercise and excessive sweating, skin irritation caused by wool and fibers, food, drugs, house dust, animal hair, irritant chemicals, and inflammation or mental stress, causes and factors that cause atopic dermatitis have also been diversified.

To prevent and improve atopic dermatitis, a method of applying an anti-allergic agent or antimicrobial agent to the skin where atopic dermatitis occurs is used to alleviate symptoms. Also, by removing factors that can cause itching in advance, treatment for preventing aggravation of symptoms of atopic dermatitis is performed.

For example, atopic dermatitis is treated by applying a steroid anti-inflammatory drug to the skin where atopic dermatitis occurs for the improvement of symptoms, by avoiding caffeine, alcohol, and heady condiments for diet adjustment, by improving environmental factors, and by relieving stress.

However, if the steroid anti-inflammatory drug is used for a long time on a soft skin area, side effects, such as thinning of the skin or skin discoloration, may be caused.

In addition, when the aggravation of symptoms of atopic dermatitis is prevented by controlling food or relieving stress, patients with atopic dermatitis may have problems with nutrition management. The symptoms of atopic dermatitis may be temporarily relieved, but it is difficult to achieve fundamental prevention and improvement of atopic dermatitis.

Therefore, research and development of effective therapeutic agents for atopic dermatitis are required.

DETAILED DESCRIPTION OF THE INVENTION

Technical Problem

Therefore, the present invention provides a composition for preventing or treating atopic dermatitis, the composition being able to effectively alleviate atopic dermatitis symptoms.

Technical Solution

To achieve the technical problem above, the present invention provides a pharmaceutical composition for preventing or treating atopic dermatitis, the pharmaceutical composition including, as an active ingredient, X-shaped DNA formed by complementary binding of oligonucleotides having nucleotide sequences of SEQ ID NO: 1 to SEQ ID NO: 4.

Furthermore, the present invention provides a health food for preventing or treating atopic dermatitis, the health food including, as an active ingredient, X-shaped DNA formed by complementary binding of oligonucleotides having nucleotide sequences of SEQ ID NO: 1 to SEQ ID NO: 4.

Furthermore, the present invention provides a cosmetic composition for preventing or treating atopic dermatitis, the cosmetic composition including, as an active ingredient, X-shaped DNA formed by complementary binding of oligonucleotides having nucleotide sequences of SEQ ID NO: 1 to SEQ ID NO: 4.

Advantageous Effects of the Invention

The present invention relates to a pharmaceutical composition for preventing or treating atopic dermatitis, the pharmaceutical composition including, as an active ingredient, X-shaped DNA formed by complementary binding of oligonucleotides having nucleotide sequences of SEQ ID NO: 1 to SEQ ID NO: 4. When the pharmaceutical composition is subcutaneously injected into an animal model of atopic dermatitis, effects of easing skin lesions, such as erythema, bleeding and edema, and the like, and ear edema, and reducing expression of immunoglobulin E (IgE) are exhibited. In this regard, the composition can be used as a pharmaceutical composition, a health food, or a cosmetic for atopic dermatitis.

BEST MODE

The inventors of the present invention have been studying the X-shaped DNA formed by complementary binding of specific four oligonucleotides. Meanwhile, it was found that the injection of the X-shaped DNA into an animal model of atopic dermatitis eases skin lesions, erythema, bleeding and edema, and the like, and ear edema and reduces expression of immunoglobulin E (IgE), thereby completing the present invention.

Hereinafter, the present invention will be described in detail.

The present invention provides a pharmaceutical composition for preventing or treating atopic dermatitis, the pharmaceutical composition including, as an active ingredient, X-shaped DNA ($X_L$-DNA) formed by complementary binding of oligonucleotides having nucleotide sequences of SEQ ID NO: 1 to SEQ ID NO: 4.

The $X_L$-DNA may form a polymer by complementary binding between two or more $X_L$-DNAs.

The $X_L$-DNA may inhibit production of immunoglobulin E (IgE) and reduce expression of thymic stromal lymphopoietin (TSLP) or thymus and activation-regulated chemokine (TARC).

The pharmaceutical composition may further include a carrier, an excipient, or a diluent conventionally used in the manufacture of the pharmaceutical composition.

Examples of a carrier, an excipient, or a diluent available in the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, or mineral oil.

The pharmaceutical composition according to the present invention can be formulated for use in the form of oral preparations, such as powders, granules, tablets, capsules, suspensions, emulsions, syrups, and aerosols, external preparations, suppositories, and sterilized injections, according to the methods known in the art.

In the case of formulation, commonly used diluents or excipients, such as fillers, extenders, binders, wetting agents, disintergrants, or surfactants, may be used. Solid formulations for oral administration may include tablets, pills, powders, granules, capsules, and the like, which may include at least one excipient, such as starch, calcium carbonate, sucrose or lactose, or gelatin.

In addition to simple excipients described above, lubricants, such as magnesium stearate and talc, may be used. Liquid formulations for oral administration may include suspensions, oral solutions, emulsions, or syrups. In addition to commonly used simple diluents, such as water and liquid paraffin, various excipients, such as wetting agents, sweeteners, fragrances, and preservatives, may be used.

Formulations for non-oral administration include sterilized aqueous solutions, non-aqueous solutions, suspensions, emulsions, freeze-drying preparations, and suppositories. Examples of the non-aqueous solutions and the suspensions include propylene glycol, polyethylene glycol, plant oil, such as olive oil, and injectable esters, such as ethyl oleate. A substrate for the suppositories includes Witepsol, Macrogol, Tween 61, cacao butter, laurin, or glycerogelatin.

A dose of the $X_L$-DNA which is the active ingredient included in the pharmaceutical composition according to the present invention may be assessed by, for example, in vivo data obtained from animal experiments using techniques well known in the art. Then, one of ordinary skill in the art can readily optimize administration to humans based on animal data.

The exact estimate, route of administration, and dosage can be selected by an individual physician in consideration of a patient's condition.

In general, a dose range of the composition to be administered to a patient may be in a range of about 0.5 mg/kg to about 1,000 mg/kg of the patient's body weight. The dosage may be provided at once or a day, or in a further series of two or more times, depending on the degree required for the patient In addition, the dosage of a compound according to the present invention may be increased or decreased depending on the route of administration, the severity of disease, and the patient's gender, weight, and age. Therefore, the dosage range is not particularly limited in any way.

The pharmaceutical composition may be administered to mammals, such as mice, rats, livestocks, and humans in various routes. Here, all methods of administration can be expected, and for example, the administration may be performed by oral, rectal or intravenous, intramuscular, subcutaneous, intratracheal inhalation, intrauterine dura mater, or intracerebroventricular injections.

Furthermore, the present invention provides a health food for preventing or treating atopic dermatitis, the health food including, as an active ingredient, X-shaped DNA formed by complementary binding of oligonucleotides having nucleotide sequences of SEQ ID NO: 1 to SEQ ID NO: 4.

The $X_L$-DNA may form a polymer by complementary binding between two or more $X_L$-DNAs.

The health food may be provided in the form of powders, granules, tablets, capsules, syrups, or drinks. In addition to the $X_L$-DNA which is the active ingredient included the health food, other foods or food additives may be included together and suitable used according to conventional methods. An amount of the active ingredient to be mixed can be determined according to intended use, for example, health or therapeutic treatment.

An effective dose of the $X_L$-DNA included in the health food may be determined according to the effective dose of the pharmaceutical composition. However, for the purpose of health and hygiene or in the case of long-term intake for health control, the effective dose of the active ingredient may be less than the range above. Since there is no problem in terms of safety, the active ingredient can be obviously used in an amount exceeding the range above.

Types of the health food are not particularly limited, and examples thereof include meet, sausage, bread, chocolate, candy, snack, cracker, pizza, ramen and other noodles, gum, and dairy products including ice cream, various soups, drinks, tea, beverage, alcoholic beverage, and vitamin complex.

In addition, the present invention provides a functional cosmetic composition for preventing or treating atopic dermatitis, the functional cosmetic composition including, as an active ingredient, X-shaped DNA formed by complementary binding of oligonucleotides having nucleotide sequences of SEQ ID NO: 1 to SEQ ID NO: 4.

The $X_L$-DNA may form a polymer by complementary binding between two or more $X_L$-DNAs.

The functional cosmetic composition may be provided for use as an ointment for external use, a basic cosmetic, a make-up cosmetic, a body cosmetic, or a shaving cosmetic. Examples of the basic cosmetic include an essence, a lotion, a cream, a gel, a skin toner, a pack, a massage cream, and an emulsion. Examples of the make-up cosmetic include a foundation, a lipstick, an eye shadow, an eye liner, a mascara, an eyebrow pencil, and a make-up base. Examples of the body cosmetic include a soap, a liquid cleaner, a bath salt, a sunscreen cream, and a sun oil. Examples of the shaving cosmetics include an aftershave lotion and a shaving cream.

In addition to the $X_L$-DNA which is the active ingredient included the functional cosmetic composition, an excipient or a diluent may be further included for the improvement of a functional material or a physical property thereof.

In an embodiment, to improve physical properties, the functional cosmetic composition may further include flavoring matters, coloring matters, bactericides, antioxidants, preservatives, moisturizers, thickeners, inorganic materials, or synthetic macromolecules. Additional ingredients to be mixed may include oil and fat components, emollient matters, surfactants, organic pigments, inorganic pigments, organic particulate materials, ultraviolet ray absorbers, pH adjusters, alcohols, blood circulation catalysts, cooling matters, anhydrotics, or purified water.

Ingredients to be mixed in addition to the active ingredient are not particularly limited. Any ingredient can be mixed within a range not to impair the purpose and effect of the present invention.

In addition, the functional cosmetic composition may be prepared in the form of solutions, emulsions, or viscous mixtures, or in any form of the conventional formulations in the art, such as a spray, an emulsion, a cream, a lotion, a skin toner, a pack, a foundation, a lotion, a cosmetic solution, or a hair cosmetic.

In detail, the functional cosmetic composition of the present invention may be formulated in the form of a spray, a soap, a cleansing foam, a cleansing lotion, a cleansing body cream, a body lotion, a body cleanser, a skin lotion, a skin softener, a skin toner, an astringent lotion, a milk lotion, a moisturizing lotion, a nutrient lotion, a massage cream, a nutrient cream, a moisturizing cream, a hand cream, a foundation, an essence, a nutrient essence, and a pack.

In an embodiment, when the functional cosmetic composition of the present invention is formulated in the form of powder or spray, as a carrier component, lactose, talc, silica, aluminum hydroxide, calcium silicate, or polyamide powder may be used. In particular, when the functional cosmetic composition of the present invention is formulated in the form of spray, a propellant, such chlorofluorohydrocarbon, propane/butane, or dimethyl ether, may be further included.

When the functional cosmetic composition of the present invention is formulated in the form of paste, cream, or gel, as a carrier component, animal fiber, plant fiber, wax, paraffin, starch, tragacanth, cellulose derivative, polyethylene glycol, silicon, bentonite, silica, talc, or zinc oxide may be used.

When the functional cosmetic composition of the present invention is formulated in the form of a solution or emulsion, as a carrier component, a solvent, a salvation material, or a demulsifier may be used, and for example, water, ethanol, isopropanol, ethyl carbonate, ethyl acetate, benzyl alcohol, benzyl benzoate, 1,3-butylglycol oil, glycerol aliphatic ester, polyethylene glycol, or fatty acid ester of sorbitan may be used.

When the functional cosmetic composition of the present invention is formulated in the form of a suspension, as a carrier component, a liquid diluent, such as water, ethanol, or propylene glycol, a suspension component, such as ethoxylated isostearyl alcohol, polyoxyethylene sorbitol ester, or polyoxyethylene sorbitan ester, microcrystalline cellulose, aluminum metahydroxide, bentonite, agar, or tragacanth may be used.

When the functional cosmetic composition of the present invention is formulated in the form of a surfactant-containing cleansing, as a carrier component, aliphatic alcohol sulfate, aliphatic alcohol ether sulfate, sulfosuccinic acid monoester, isethionate, imidazolinium derivative, methyl taurate, sarco cyanate, fatty acid amide ether sulfate, alkylamido betaine, aliphatic alcohol, fatty acid glyceride, fatty acid diethanolamide, vegetable oil, lanolin derivative, or ethoxylated glycerol fatty acid ester may be used.

MODE OF THE INVENTION

Hereinafter, the present invention will be described in more detail with reference to the following examples. However, the present invention is not limited to these examples.

<Example 1> Test Protocol

1. Preparation of $X_L$-DNA

Four oligonucleotides shown in Table 1 were dissolved in the same amount in an annealing buffer (10 mM Tris-HCl, pH 8.0, 1 mM EDTA, 50 mM NaCl), and sterilized Milli-Q water was added thereto to have a final concentration of 0.1 mM. The mixture of the oligonucleotides was annealed by heating to a temperature of 95° C. using a thermal cycler, and then, slowly cooling to a temperature of 4° C.

TABLE 1

| | Nucleotide sequence |
|---|---|
| $X_L$-DNA | X01: 5'-ACG TCG ACC GAT GAA TAG CGG TCA GAT CCG TAC CTA CTC G-3' (SEQ ID NO: 1) |
| | X02: 5'-ACG TCG AGT AGG TAC GGA TCT GCG TAT TGC GAA CGA CTC G-3' (SEQ ID NO: 2) |
| | X03: 5'-ACG TCG AGT CGT TCG CAA TAC GGC TGT ACG TAT GGT CTC G-3' (SEQ ID NO: 3) |
| | X04: 5'-ACG TCG AGA CCA TAC GTA CAG CAC CGC TAT TCA TCG GTC G-3' (SEQ ID NO: 4) |

Figure 1:
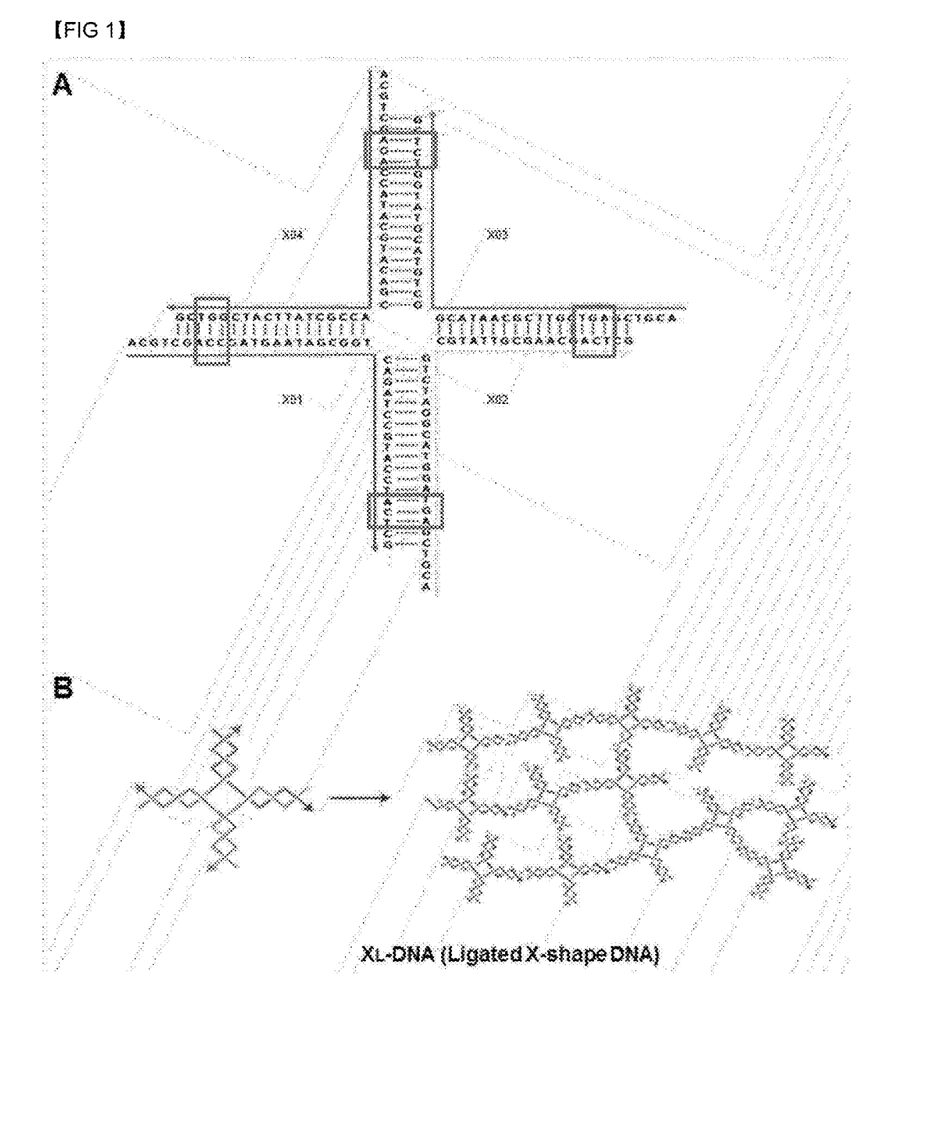
FIG. 1 is a schematic diagram showing the $X_L$-DNA structure.

The $X_L$-DNA has a structure shown in FIG. 1A, wherein ACC of X01 and GGT of X04, AGT of X02 and ACT of X01, AGT of X03 and ACT of X02, and AGA of X04 and TCT of X03 were complementarily linked.

Therefore, as shown in FIG. 1B, the $X_L$-DNA is able to present as an aggregated complex in which monomers were linked together.

The $X_L$-DNA was analyzed by 6% polyacrylamide gel electrophoresis (PAGE) at a voltage of 200 V for 20 minutes at room temperature, and then, visualized by staining with ethidium bromide.

For cellular uptake study, Alexa Fluor 488-labelled mTri-2 was used instead of the mTri-2.

2. Reagents

House dust mite (HDM) was obtained from Biostri Inc. (Kobe, Japan), dieckol was purchased from Botamedi Inc. (Jeju, Korea), 1-chloro-2,4-dinitrobenzene (DNCB) was purchased from Sigma (St. Louis, Mo.), aceton was purchased from Merck (Darmstadt, Germany), and Veet was purchased from Reckitt Benkiser (Mannheim, Germany).

3. Animal for Experiment

Male NC/Nga mice (body weight: 14 g to 22 g, 4 weeks old) were purchased from Central Lab Inc. (Seoul, Korea) and the branch of Charles River Japan (Kanagawa, Japan), and were raised in a controlled environment (temperature: 22±2° C.; lighting duration: 07:00-19:00 h, and humidity: 30%-70%) under specific pathogen-free (SPF) conditions. The animals were freely supplied with food and water, and after 2 weeks of adaptation, the experimental groups were randomly divided into three groups.

The animal experiments performed in the present study were approved by the Institutional Animal Care and Use Committee of School of Medicine of the Catholic University (Approval No: #2013-020-01).

4. Occurrence of Atopic Dermatitis (AD)

The male NC/Nga mice were stimulated with HDM, and 1% 2,4-dinitrochlorobenzene (DNCB, a mixture of 200 μl of acetone and olive oil at a ratio of 3:1) (at intervals of 0, 7, 14, 21, 28, and 35 days). After one day, 7.5 mg of the $X_L$-DNA was injected subcutaneously into the $X_L$-DNA mouse groups every day while a phosphate buffer solution (PBS) was injected subcutaneously into to the control mouse group. Here, no stimulation was given to the normal mice.

After 42 days, all the mice were euthanized, and skin and blood thereof were extracted.

5. Evaluation of Severity of Dermatitis

The severity of clinical dermatitis was tested by well-known methods (see Sone, K., et al., Exp Anim, 2007. 56(2): p. 139-48). The severity of dermatitis was evaluated once a week. The progression of erythema/hemorrhage, scarring/ dryness, edema, and excoriation/erosion was evaluated with scores as follows: 0: none, 1: light (<20%), 2: medium (20% to 60%), and 3: severe (>60%). The sum of scores was used as the score of dermatitis.

6. Histological Analysis of Skin Lesions

After the mice were euthanized, skin samples were collected from the back and ear of the mice.

Each of the samples was fixed with 10% buffered formalin, embedded in paraffin, and then, cut into 4 μm pieces. The pieces were stained with hematoxylin and eosin (H&E). Afterwards, pathological changes, such as epidermal and dermal hyperplasia, parakeratosis, hyperkeratosis, dermal edema, vesicular formation, and inflammation, were compared between groups.

To evaluate infiltration of mast cells, selected fragments were stained with toluidine blue. The number of mast cells in 20 fragments of each sample was measured using the density of mast cells per square millimeter.

7. Measurement of Ear Thickness

The ear thickness was measured using a micrometer (Mitutoyo, Kawasaki, Japan).

The micrometer used herein was applied to the tip of the ear away from the ear cartilage ridge, and the thickness measured on the micrometer was recorded.

8. Enzyme-Linked Immunosorbent Assay (ELISA)

The blood samples of each mouse collected in Example 1-4 were centrifuged at a speed of about 1,700 g for 30 minutes, to thereby obtain serum therefrom. The obtained serum was stored at a temperature of −70° C.

The total IgE level in the serum was measured using an IgE ELISA kit (Shibayagi Co., Ltd., Gunma, Japan).

9. Quantitative Polymerase Chain Reaction (PCR)

First, total RNAs were extracted from skin tissues using a Welprep total RNA isolation reagent (Welgene, Daegu, Korea).

1 μg of total RNAs were reverse transcribed according to a reverse transcription PCR (20 μl, RT-PCR, Promega, Madison, Wis.).

The real-time quantitative PCR and result analysis obtained therefrom was performed using iQ5 (Bio-rad, Hercules, Calif.).

The expression of thymic stromal lymphopoietin (TSLP) mRNA was normalized to RNA loading for each sample using mouse actin mRNA as an internal standard.

[TSLP primer, forward: 5'-GGACCACTG GTGTTTAT-TCT-3' (SEQ ID NO: 5); reverse: 5'-CAGGGTTTAG ATGCTGTCAT-3' (SEQ ID NO: 6)], [T-box-containing protein expressed in T cells (T-bet) primer, forward: 5'-TACGCATCTG TTGATACGAG-3' (SEQ ID NO: 7); reverse: 5'-TTCATAACTG TGTTCCCGAG-3' (SEQ ID NO: 8)], [Trans-acting T-cell-specific transcription factor (GATA3) primer, forward: 5-ATGAGAAAGA GTGCCT-CAAG-3' (SEQ ID NO: 9); reverse: 5'-CTTCTGTGCT GGATCGTG-3' (SEQ ID NO: 10)], [Actin primer, forward: 5'-TCATGAAGTG TGACGTTGAC ATCCGT-3' (SEQ ID NO: 11); reverse: 5'-TTGCGGGCAC GATGGAGGGG CCGGA-3' (SEQ ID NO: 12)] were each used to amplify 152 bp and 452 bp fragments.

The PCR conditions are as follows: In the case of TSLP, 40 cycles each consisting of amplification at 95° C. for 10 seconds, at 60° C. for 10 seconds, and at 72° C. for 7 seconds; in the case of glyceraldehyde-3-phosphate dehydrogenase (GAPDH), 30 cycles each consisting of amplification at 95° C. for 10 seconds, at 64° C. for 10 seconds, and at 72° C. for 18 seconds.

All PCR conditions were performed according to the melting curve analysis.

<Example 2> Effect of $X_L$-DNA on Atopic Skin Lesions Induced by HDM/DNCB of NC/Nga Mice The NC/Nga mice with AD suffered from itching, eczema, inflammatory skin lesions, and ear thickening.

To establish a model of atopic dermatitis induced by an HDM antigen in the NC/Nga mice, HDM/DNCB was repeatedly administered to skin lesions and ears twice a week for 6 weeks.

Figure 2:
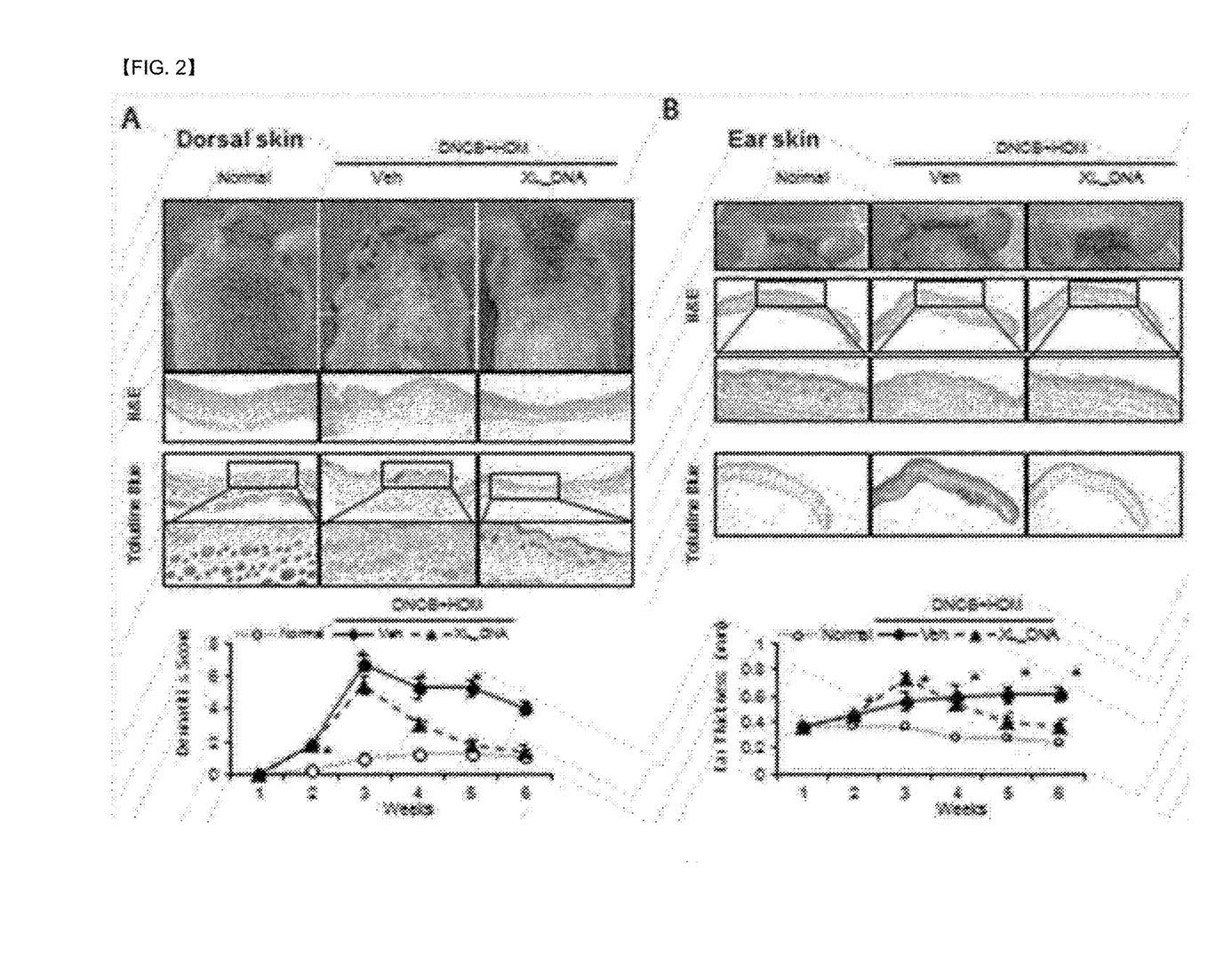
FIG. 2 shows the results regarding effects of $X_L$-DNA on the atopic skin lesions of an NC/Nga mouse induced by house dust mite (HDM)/2,4-dinitrochlorobenzene (DNCB).

As a result, the repeated administration of HDM/DNCB in the control NC/Nga mice first induced skin dryness, followed by severe erythema, hemorrhage, scar, edema, exfoliation, and rash (see FIG. 2A).

However, $X_L$-DNA therapy inhibited such skin symptoms. Furthermore, in comparison with the normal group, the histologic features of skin lesions in the control group showed accumulation of inflammatory cells in the dermis/ epidermis, edema, and skin thickening, whereas the $X_L$-DNA-treated group showed a decrease in these changes.

The skin conditions were evaluated once a week for 6 weeks using a dermatitis scoring metric. The dermatitis score of the control group was significantly different from that of the normal group at the third week, and rapidly increased.

However, the $X_L$-DNA-treated group showed a significant decrease in the dermatitis score at the fourth week compared to the control mice.

<Example 3> Effect of $X_L$-DNA on Ear Edema Induced by HDM/DNCB in NC/Nga Mice

In the NC/Nga mice, the administration of HDM/DNCB gradually increased ear edema.

When compared to the normal group, the accumulation of inflammatory cells in the ear and histologic features of the hypertrophy of the dermis and epidermis of the control group were shown (see FIG. 2B).

However, in the $X_L$-DNA-treated mice, it was observed that the infiltration of inflammatory cells into the dermis and thickening of the dermis/epidermis were reduced.

At the fifth week, it was observed that the ear edema of the control group significantly increased compared to the normal group, whereas the treatment of $X_L$-DNA significantly reduced the ear edema, which was increased by HDM/DNCB, at the fifth to sixth week.

<Example 4> Effect of $X_L$-DNA on Infiltration of Inflammatory Cells and IgE Free Induced by HDM/DNCB of NC/Nga Mice Mast cells are known to be important functional groups of IgE-mediated allergic diseases, and an increase in the IgE levels in the serum is an important feature of AD.

Figure 3:
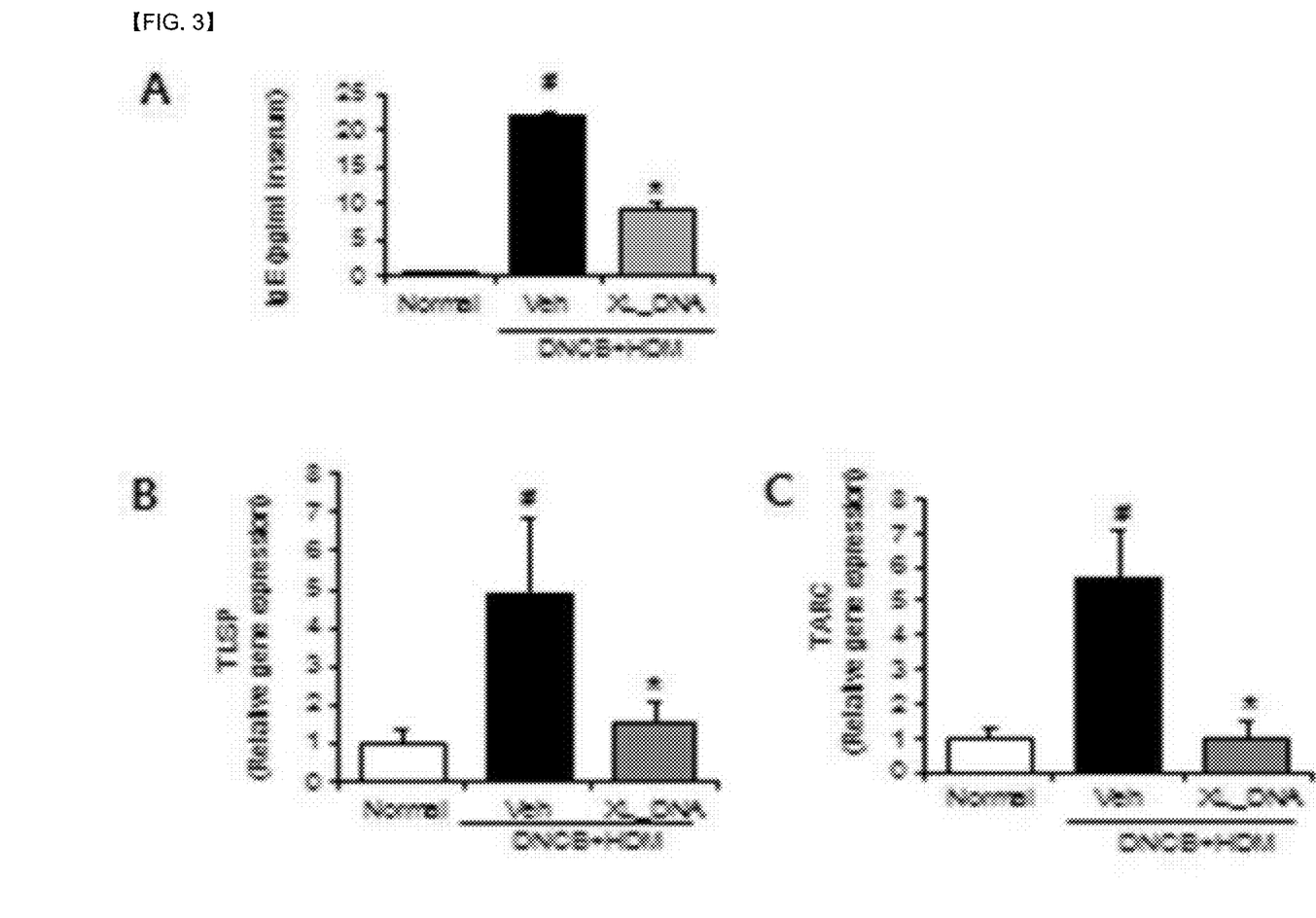
FIG. 3 shows the results regarding effects of $X_L$-DNA in the production of HDM/DNCB-induced inflammation mediators of the NC/Nga mouse.

The treatment of HDM/DNCB in the control group significantly increased the IgE level in the serum compared to the normal mice, whereas the treatment of $X_L$-DNA significantly reduced the IgE level in the serum (see FIG. 3A).

TSLP has an important role in the suitable Th2 immune initiation system for the progression of AD, and is related to the Th2 immune response and induction associated with TARC and IgE.

According to the quantitative reverse transcription-polymerase chain reaction (qRT-PCR) analysis, the $X_L$-DNA in the NC/Nga mice showed significant downward adjustment in the expression and production of mRNA of the TSLP and TARC induced by HDM/DNCB (see FIGS. 3B and 3C).

Such results showed that the $X_L$-DNA inhibits the Th2 response in the NC/Nga mouse models and accordingly inhibits dermatitis induced by HDM/DNCB.

The invention claimed is:

1. A method of preventing or treating atopic dermatitis in a subject in need thereof, the method comprising:
   providing a pharmaceutical composition comprising X-shaped DNA ($X_L$-DNA) formed by complementary binding of oligonucleotides having the nucleotide sequence of SEQ ID NO: 1 to SEQ ID NO: 4 as an active ingredient; and
   administering the pharmaceutical composition to the subject, wherein the atopic dermatitis is prevented or treated.

2. The method of claim 1, wherein the $X_L$-DNA forms a polymer by complementary binding between two or more $X_L$-DNAs.

3. The method of claim 2, wherein the $X_L$-DNA inhibits production of immunoglobulin E (IgE).

4. The method of claim 1, wherein the $X_L$-DNA reduces expression of thymic stromal lymphopoietin (TSLP) or thymus and activation-regulated chemokine (TARC).

5. A health food for preventing or treating atopic dermatitis, the health food comprising, as an active ingredient, X-shaped DNA formed by complementary binding of oligonucleotides having nucleotide sequences of SEQ ID NO: 1 to SEQ ID NO: 4.

6. The health food of claim 5, wherein the X-shaped DNA forms a polymer by complementary binding between two or more $X_L$-DNAs.

7. A method of preventing or treating atopic dermatitis in a subject in need thereof, the method comprising:
   providing a cosmetic composition comprising X-shaped DNA formed by complementary binding of oligonucleotides having the nucleotide sequence of SEQ ID NO: 1 to SEQ ID NO: 4 as an active ingredient; and
   administering the cosmetic composition to the subject, wherein the atopic dermatitis is prevented or treated.

8. The method of claim 7, wherein the X-shaped DNA forms a polymer by complementary binding between two or more $X_L$-DNAs.

* * * * *

SEQUENCE LISTING

```
<160> NUMBER OF SEQ ID NOS: 12

<210> SEQ ID NO 1
<211> LENGTH: 40
<212> TYPE: DNA
<213> ORGANISM: Artificial Sequence
<220> FEATURE:
<223> OTHER INFORMATION: X01 DNA

<400> SEQUENCE: 1
acgtcgaccg atgaatagcg gtcagatccg tacctactcg                              40

<210> SEQ ID NO 2
<211> LENGTH: 40
<212> TYPE: DNA
<213> ORGANISM: Artificial Sequence
<220> FEATURE:
<223> OTHER INFORMATION: X02 DNA

<400> SEQUENCE: 2
acgtcgagta ggtacggatc tgcgtattgc gaacgactcg                              40

<210> SEQ ID NO 3
<211> LENGTH: 40
<212> TYPE: DNA
<213> ORGANISM: Artificial Sequence
<220> FEATURE:
<223> OTHER INFORMATION: X03 DNA

<400> SEQUENCE: 3
acgtcgagtc gttcgcaata cggctgtacg tatggtctcg                              40

<210> SEQ ID NO 4
<211> LENGTH: 40
<212> TYPE: DNA
<213> ORGANISM: Artificial Sequence
<220> FEATURE:
<223> OTHER INFORMATION: X04 DNA

<400> SEQUENCE: 4
acgtcgagac catacgtaca gcaccgctat tcatcggtcg                              40

<210> SEQ ID NO 5
<211> LENGTH: 20
<212> TYPE: DNA
<213> ORGANISM: Artificial Sequence
<220> FEATURE:
<223> OTHER INFORMATION: TSLP forward primer

<400> SEQUENCE: 5
ggaccactgg tgtttattct                                                    20
```

```
<210> SEQ ID NO 6
<211> LENGTH: 20
<212> TYPE: DNA
<213> ORGANISM: Artificial Sequence
<220> FEATURE:
<223> OTHER INFORMATION: TSLP reverse primer

<400> SEQUENCE: 6
cagggtttag atgctgtcat                                              20

<210> SEQ ID NO 7
<211> LENGTH: 20
<212> TYPE: DNA
<213> ORGANISM: Artificial Sequence
<220> FEATURE:
<223> OTHER INFORMATION: T-bet forward primer

<400> SEQUENCE: 7
tacgcatctg ttgatacgag                                              20

<210> SEQ ID NO 8
<211> LENGTH: 20
<212> TYPE: DNA
<213> ORGANISM: Artificial Sequence
<220> FEATURE:
<223> OTHER INFORMATION: T-bet reverse primer

<400> SEQUENCE: 8
ttcataactg tgttcccgag                                              20

<210> SEQ ID NO 9
<211> LENGTH: 20
<212> TYPE: DNA
<213> ORGANISM: Artificial Sequence
<220> FEATURE:
<223> OTHER INFORMATION: GATA3 forward primer

<400> SEQUENCE: 9
atgagaaaga gtgcctcaag                                              20

<210> SEQ ID NO 10
<211> LENGTH: 18
<212> TYPE: DNA
<213> ORGANISM: Artificial Sequence
<220> FEATURE:
<223> OTHER INFORMATION: GATA3 reverse primer

<400> SEQUENCE: 10
cttctgtgct ggatcgtg                                                18

<210> SEQ ID NO 11
<211> LENGTH: 26
<212> TYPE: DNA
<213> ORGANISM: Artificial Sequence
<220> FEATURE:
<223> OTHER INFORMATION: actin forward primer

<400> SEQUENCE: 11
tcatgaagtg tgacgttgac atccgt                                       26

<210> SEQ ID NO 12
<211> LENGTH: 25
<212> TYPE: DNA
<213> ORGANISM: Artificial Sequence
<220> FEATURE:
<223> OTHER INFORMATION: actin reverse primer
```

-continued

```
<400> SEQUENCE: 12
ttgcgggcac gatggagggg ccgga                                              25
```